United States Patent
Inan (10) Patent No.: US 11,518,941 B2
(45) Date of Patent: Dec. 6, 2022

(54) PYROLYSIS TO DETERMINE HYDROCARBON EXPULSION EFFICIENCY OF HYDROCARBON SOURCE ROCK

(71) Applicant: Saudi Arabian Oil Company, Dhahran (SA)

(72) Inventor: Sedat Inan, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 16/841,561

(22) Filed: Apr. 6, 2020

(65) Prior Publication Data
US 2020/0231877 A1 Jul. 23, 2020

Related U.S. Application Data

(60) Division of application No. 15/637,932, filed on Jun. 29, 2017, now Pat. No. 10,611,967, which is a (Continued)

(51) Int. Cl.
*C10B 53/06* (2006.01)
*C10G 9/18* (2006.01)
(Continued)

(52) U.S. Cl.
CPC ............... *C10B 53/06* (2013.01); *B01J 6/008* (2013.01); *C10G 9/18* (2013.01); *G01N 1/286* (2013.01);
(Continued)

(58) Field of Classification Search
CPC .......... G01N 33/241; G01N 2030/121; G01N 2030/123; G01N 2030/125; G01N 30/12;
(Continued)

(56) References Cited

U.S. PATENT DOCUMENTS 2,114,416 A * 4/1938 Donnelly ............... C10B 55/04
201/28
4,287,752 A 9/1981 Ury
(Continued)

FOREIGN PATENT DOCUMENTS

CN 1030091 1/1989
CN 1320147 10/2001
(Continued)

OTHER PUBLICATIONS

Jorge et al, Analysis of Volatiles in Fluid Inclusions by Direct online Crushing Mass Spectrometry, Journal of the Brazilian Chemical Society • Mar. 2011 (Year: 2011).*
(Continued)

*Primary Examiner* — David L Singer
(74) *Attorney, Agent, or Firm* — Fish & Richardson P.C.

(57) ABSTRACT

An open system pyrolysis of a first hydrocarbon source rock sample obtained from a natural system is performed within a pyrolysis chamber by maintaining the pyrolysis chamber at a substantially constant temperature. Hydrocarbons are recovered from the pyrolysis chamber released by the first hydrocarbon source rock sample. A thermo-vaporization is performed within the pyrolysis chamber on the pyrolyzed sample at a substantially constant temperature. A first hydrocarbon expulsion efficiency of hydrocarbon source rock is determined. A second hydrocarbon rock sample is ground to a grain size less than or equal to or less than 250 micrometers. A second pyrolysis is performed on the ground hydrocarbon source rock sample by maintaining the chamber at a substantially constant temperature. A second hydrocarbon expulsion efficiency of the hydrocarbon source rock in the natural system is determined. The first hydrocarbon expulsion efficiency is verified using the second hydrocarbon expulsion efficiency.

4 Claims, 5 Drawing Sheets

Related U.S. Application Data continuation-in-part of application No. 14/717,825, filed on May 20, 2015, now abandoned.

(51) Int. Cl.

| | |
|---|---|
| *B01J 6/00* | (2006.01) |
| *G01N 33/24* | (2006.01) |
| *G01N 1/28* | (2006.01) |
| *G01N 1/40* | (2006.01) |
| *G01N 31/12* | (2006.01) |
| *G01N 30/12* | (2006.01) |
| *G01N 30/72* | (2006.01) |
| *G01N 30/86* | (2006.01) |

(52) U.S. Cl.
CPC ......... *G01N 1/4022* (2013.01); *G01N 33/241* (2013.01); *G01N 30/12* (2013.01); *G01N 30/7206* (2013.01); *G01N 30/8679* (2013.01); *G01N 31/12* (2013.01); *G01N 33/24* (2013.01); *G01N 2001/2866* (2013.01); *G01N 2001/4033* (2013.01); *G01N 2030/123* (2013.01); *G01N 2030/125* (2013.01)

(58) Field of Classification Search
CPC ........... G01N 30/7206; G01N 30/8679; G01N 31/12; G01N 33/24; E21B 49/00; B01J 6/008; C10B 53/06; C10G 9/18
USPC ................................ 73/23.38, 19.02, 152.13
See application file for complete search history.

(56) References Cited

U.S. PATENT DOCUMENTS

| | | | |
|---|---|---|---|
| 4,325,907 | A | 4/1982 | Dembicki, Jr. |
| 4,861,263 | A | 8/1989 | Schirmer |
| 5,201,219 | A | 4/1993 | Bandurski et al. |
| 5,363,692 | A | 11/1994 | Lafargue |
| 5,997,819 | A | 12/1999 | Mougin |
| 2003/0098149 | A1* | 5/2003 | Wellington .............. E21B 43/24 166/52 |
| 2009/0306898 | A1* | 12/2009 | Anschutz .................. G01N 3/10 702/11 |
| 2010/0101304 | A1 | 4/2010 | McIntyre |
| 2010/0155078 | A1 | 6/2010 | Walters et al. |
| 2013/0245345 | A1* | 9/2013 | Hutchon .................. C10B 53/07 585/240 |
| 2014/0290334 | A1 | 10/2014 | Friedrich |
| 2017/0074852 | A1 | 3/2017 | Nguyen |

FOREIGN PATENT DOCUMENTS

| | | |
|---|---|---|
| CN | 1796491 | 7/2006 |
| CN | 1957065 | 5/2007 |
| CN | 101688127 | 3/2010 |
| CN | 102119327 | 7/2011 |
| CN | 104298883 | 1/2015 |
| CN | 106056459 | 10/2016 |
| CN | 106796210 | 5/2017 |
| EP | 2727661 | 5/2014 |
| FR | 2675581 | 10/1992 |
| GB | 1577967 | 10/1980 |
| GB | 2161269 | 1/1986 |
| WO | 2016186689 | 11/2016 |

OTHER PUBLICATIONS

PCT International Search Report and Written Opinion of the International Searching Authority, PCT/US2015/059147, dated Feb. 17, 2016, 13 pages.
International Search Report and Written Opinion issued in International Application No. PCT/US2018/038799 dated Dec. 4, 2018, 14 pages.
Gulf Cooperation Council Examination Report issued in GCC Application No. 2016-31169 dated May 30, 2018, 5 pages.
Al-Ayed et al, Pyrolysis of Ellajjun Oil Shale and Particle Size Effect on Product Components, 2009, International Renewable Energy Congress Nov. 5-7, 2009—Sousse Tunisia.
Atmaram et al., "Gas reservoir characteristics of the Lower Gondwana Shales in Raniganj Basin of Eastern India," Journal of Petroleum Science and Engineering, vol. 149, Nov. 16, 2016, 16 pages.
Behar et al, Rock-Eval 6 Technology: Performances and Developments, 2001, Oil & Gas Science and Technology—Rev. IFP, vol. 56 (2001), No. 2, pp. 111-134.
Behar et al., "Themal Cracking of Kerogen in Open and Closed Systems: Determination of Kinetic Parameters and Stoichiometric Coefficients for Oil and Gas Generation", Org. Geochem., vol. 26, published in 1997, pp. 321-339.
Cornford, "Risking Petroleum Systems", AAAPG 2000, Proceedings of the Fifth International Conference and Exhibition on Petroleum Geochemistry and Exploration in the Afro-Asian Region, Jan. 1, 2000, 4 pages.
Eseme et al., "Experimental Investigation of the Compositional Variation of Petroleum during Primary Migration", Science Direct, Organic Geochemistry, vol. 38, No. 8, Jul. 29, 2007, pp. 1373-1397.
Horsfield et al, On the Atypical Petroleum-Generating Characteristics of Alginite in the Cambrian Alum Shale, 1992, M. Schidlowski et al. (Eds.) Early Organic Evolution: Implications for Mineral and Energy Resources Springer-Verlag Berlin Heidelberg 1992.
Horsfield et al., "Some Potential Applications of Pyrolysis to Basin Studies", J. Geol. Soc. London, vol. 140, published in 1983, pp. 431-443.
Horsfield et al., "The Micro-Scale Simulation of Maturation: Outline of a New Technique and its Potential Applications", Geologische Rundschau, Published in 1989, pp. 361-374.
Inan et al., "Expulsion of Oil from Petroleum Source Rocks: Inferences from Pyrolysis of Samples of Unconventional Grain Size", Org. Geochem. vol. 29, No. 1-3, Published in 1998, pp. 45-61.
Inan, "Gaseous Hydrocarbons Generated during Pyrolysis of Petroleum Source Rocks using Unconventional Grain-Size: Implications for Natural Gas Composition", Organic Geochemistry, published in 2000, pp. 1409-1418.
Khalil Oil Shale Pyrolysis and Effect of Particle Size on the Composition of Shale Oil, 2013, Oil Shale, 2013, vol. 30, No. 2, pp. 136-146.
Lafargue et al, Rock-Eval 6 Applications in Hydrocarbon Exploration, Production, and Soil Contamination Studies, 1998, Revue De L'Institut Francais Du Petrole vol. 53, N° 4, Juillet-Aout 1998.
Lewan et al., "Comparison of Petroleum Generation Kinetics by Isothermal Hydrous and Nonisothermal Open-System Pyrolysis", Organic Geochemistry 33, Published in 2002, pp. 1457-1475.
Mansuy et al, Importance of the Reacting Medium in Artificial Maturation of a Coal by Confined Pyrolysis. 1. Hydrocarbons and Polar Compounds, 1995, Energy & Fuels 1995,9, 691-703.
McCarthy et al, Basic Petroleum Geochemistry for Source Rock Evaluation, 2011, Oilfield Review Summer 2011: 23, No. 2.
Oja, Vaporization Parameters of Primary Pyrolysis Oil From Kukersite Oil Shale, Feb. 3, 2015, Oil Shale, 2015, vol. 32, No. 2, pp. 124-133.
Pankow, Cold Trapping of Volatile Organic Compounds on Fused Silica Capillary Columns, 1983, Dr. Alfred Huethig Publishers, Journal of High Resolution Chromatography & Chromatography Communications vol. 6, Jun. 1983.
Peters et al, Petroleum generation kinetics: Single versus multiple heatingramp open-system pyrolysis, Apr. 2015, AAPG Bulletin, v. 99, No. 4 (Apr. 2015), pp. 591-616.
Solar Energy Research Institute for the U.S. Department of Energy, Specialists Workshop on Fast Pyrolysis of Biomass Proceedings, 1980.
Weng et al, Characterization of oil generation and expulsion from coals and source rocks using diamond anvil cell pyrolysis, 2003, Organic Geochemistry 34 (2003) 771-787.
Parhizgar et al., "Modeling of vaporization enthalpies of petroleum fractions and pure hydrocarbon using genetic programming," Journal of Petroleum Science and Engineering, 2013, 112:97-104, 8 pages.

(56) References Cited

OTHER PUBLICATIONS

CN Office Action in Chinese Appln. No. 201880043605.5, dated Mar. 3, 2022, 11 pages, with English Translation.

* cited by examiner

FIG. 5B

PYROLYSIS TO DETERMINE HYDROCARBON EXPULSION EFFICIENCY OF HYDROCARBON SOURCE ROCK

CROSS-REFERENCE TO RELATED APPLICATION

This application is a divisional of U.S. patent application Ser. No. 15/637,932 filed on Jun. 29, 2017, which is a continuation-in-part of U.S. patent application Ser. No. 14/717,825 filed on May 20, 2015, both of which are incorporated by reference herein in their entirety.

TECHNICAL FIELD

This specification relates to analyzing rock in which hydrocarbon is generated and trapped.

BACKGROUND

Hydrocarbon exploration techniques sometimes involve generating computer-generated geological models and calibrating such models using experimental data. For example, the experimental data can be provided as inputs to the geological models. The experimental data can be obtained from laboratory experiments performed on hydrocarbon source rock, that is, rock in which hydrocarbons are generated. The accuracy of the predictions of computer-generated models can depend on the quality of the calibration of the models using measured experimental data, which, in turn, can depend on the conditions under which the laboratory experiments are performed. Said differently, the quality of the experimental data can be high if the conditions under which the laboratory experiments are performed are substantially similar to the conditions experienced by the rock in the subsurface from which the hydrocarbons are produced. One input to the geological model can include a characteristic of the hydrocarbon rock to expel trapped hydrocarbons. Pyrolysis is one technique to study the characteristic of hydrocarbon source rock to expel or trap hydrocarbons.

SUMMARY

This specification describes pyrolysis techniques to analyze the characteristics of a hydrocarbon source rock to expel/retain trapped hydrocarbons. In particular, for example, this specification describes pyrolysis to determine hydrocarbon expulsion efficiency of hydrocarbon source rock.

An example implementation of the subject matter described within this disclosure is a method with the following features. An open system pyrolysis of a first hydrocarbon source rock sample obtained from a natural system is performed within a pyrolysis chamber resulting in a pyrolyzed sample. The open system pyrolysis is performed by maintaining the pyrolysis chamber at a substantially constant temperature of 375° C. The first hydrocarbon source rock sample includes hydrocarbon source rocks having an equivalent spherical diameter of substantially at least one centimeter. Hydrocarbons are recovered from the pyrolysis chamber released by the first hydrocarbon source rock sample in response to the open system pyrolysis. A thermo-vaporization is performed within the pyrolysis chamber on the pyrolyzed sample on which the open system pyrolysis was performed at a substantially constant temperature of 375° C. Hydrocarbons released by the pyrolyzed sample in response to the thermo-vaporization are recovered from the pyrolysis chamber. A first hydrocarbon expulsion efficiency of hydrocarbon source rock in the natural system is determined based on the recovered hydrocarbons released by the first hydrocarbon source rock sample in response to the open system pyrolysis and based on the recovered hydrocarbons released by the pyrolyzed sample in response to thermo-vaporization. A second hydrocarbon rock sample of a pre-defined mass is ground resulting in a ground hydrocarbon source rock sample having a grain size less than or equal to or less than 250 micrometers. The grinding is performed within an integrated sample-crusher and thermo-vaporization chamber. A second pyrolysis is performed within the integrated sample-crusher and thermo-vaporization chamber on the ground hydrocarbon source rock sample. The second pyrolysis is performed by maintaining the integrated sample-crusher and thermo-vaporization chamber at a substantially constant temperature of 375° C. within the integrated sample-crusher and thermo-vaporization chamber. A second hydrocarbon expulsion efficiency of the hydrocarbon source rock in the natural system is determined based on performing the second pyrolysis on the second hydrocarbon source rock sample. The first hydrocarbon expulsion efficiency is verified using the second hydrocarbon expulsion efficiency.

Aspects of the example implementation, which can be combined with eh example implementation alone or in combination, include the following. The integrated sample-crusher and thermo-vaporization chamber include electric driven blades.

Aspects of the example implementation, which can be combined with eh example implementation alone or in combination, include the following. The pyrolysis chamber is the sample-crusher and thermo-vaporization chamber.

Aspects of the example implementation, which can be combined with eh example implementation alone or in combination, include the following. Verifying the first hydrocarbon expulsion efficiency includes comparing the first hydrocarbon expulsion efficiency to the second hydrocarbon expulsion efficiency and determining a ratio between the first hydrocarbon expulsion efficiency and the second hydrocarbon expulsion efficiency.

Aspects of the example implementation, which can be combined with eh example implementation alone or in combination, include the following. Performing the open system pyrolysis of the first hydrocarbon source rock sample obtained from a natural system includes starting the open system pyrolysis once the pyrolysis chamber is at a temperature of substantially 375° C. A constant temperature of substantially 375° C. is maintained throughout the open system pyrolysis. The open system pyrolysis is ended after a set amount of time. The temperature at the set amount of time is substantially 375° C.

Aspects of the example implementation, which can be combined with eh example implementation alone or in combination, include the following. A quantity of the second hydrocarbon source rock sample is substantially at least 100 grams.

Aspects of the example implementation, which can be combined with eh example implementation alone or in combination, include the following. Determining a first hydrocarbon expulsion efficiency (HCEE1) comprises using a first equation:

$$HCEE1 = (HC_{Pyrolysis}) \times 100 / (HC_{Pyrolysis} + HC_{Thermo\text{-}Vaporization} + HC_{CrushingThermo\text{-}Vaporization})$$

where $HC_{Pyrolysis}$ is a quantity of hydrocarbons released in response to open system pyrolysis of the hydrocarbon source rock sample, $HC_{Thermo\text{-}Vaporization}$ is a quantity of hydrocarbons released in response to first thermo-vaporization of previously pyrolyzed hydrocarbon source rock sample in the pyrolysis chamber, $HC_{CrushingThermo\text{-}Vaporization}$ is a quantity of hydrocarbons released in response to grinding and performing the second pyrolysis on the second hydrocarbon rock sample.

Aspects of the example implementation, which can be combined with eh example implementation alone or in combination, include the following. Determining a second hydrocarbon expulsion efficiency (HCEE2) comprises using a second equation:

$$HCEE2=(HC_{Pyrolysis})\times 100/HC_{PowderedSamplePyrolysis}$$

Where $HC_{Pyrolysis}$ is a quantity of hydrocarbons released in response to open system pyrolysis of the hydrocarbon source rock sample with a grain size of substantially one centimeter, $HC_{PowderedSamplePyrolysis}$ is a quantity of hydrocarbons released in response to open system pyrolysis of a powdered hydrocarbon source rock sample with a grains size substantially less than or equal to substantially 250 microns.

Aspects of the example implementation, which can be combined with eh example implementation alone or in combination, include the following. A maturity of residual organic matter is determined. The determined maturity is input into a computer-generated geological model.

An example implementation of the subject matter described within this disclosure is a system with the following features. An integrated sample-crusher and thermo-vaporization chamber is capable of retaining a hydrocarbon rock sample. A heating element is capable of heating the integrated sample-crusher and thermo-vaporization chamber. A controller is capable of controlling the heating element to a set temperature. A sensor is capable of detecting hydrocarbons released within the integrated sample-crusher and thermo-vaporization chamber.

Aspects of the example system, which can be combined with the example system alone or in combination, include the following. Controlling the heating element to a set temperature includes heating the integrated sample-crusher and thermo-vaporization chamber to a temperature of substantially 375° C. A constant temperature of substantially 375° C. is maintained within the integrated sample-crusher and thermo-vaporization chamber while the integrated sample-crusher and thermo-vaporization chamber is in use.

Aspects of the example system, which can be combined with the example system alone or in combination, include the following. The integrated sample-crusher and thermo-vaporization chamber includes electrically driven grinding blades.

Aspects of the example system, which can be combined with the example system alone or in combination, include the following. The integrated sample-crusher and thermo-vaporization chamber is capable of containing a sample size of at least 100 grams.

Aspects of the example system, which can be combined with the example system alone or in combination, include the following. The integrated sample-crusher and thermo-vaporization chamber has a volume of at least 1 liter.

An example implementation of the subject matter described within this disclosure is a second method with the following features. An open system pyrolysis is performed within a pyrolysis chamber on a hydrocarbon source rock sample that includes fragments having an equivalent spherical diameter of substantially at least one centimeter. Performing the open system pyrolysis results in a pyrolyzed rock sample. Hydrocarbons released by the rock sample in response to the open system pyrolysis are recovered. A first quantity of hydrocarbons released in response to the open system pyrolysis is determined. A thermo-vaporization is performed within the pyrolysis chamber on the pyrolyzed rock sample. Hydrocarbons released by the rock sample in the pyrolysis chamber in response to the thermo-vaporization are recovered. A second quantity of hydrocarbons released in response to thermo-vaporization in the pyrolysis chamber is determined. The sample are placed in a crushing chamber and crushing and performing thermo-vaporization on the pyrolyzed rock sample. Hydrocarbons released by the rock sample in response to crushing and thermo-vaporization are recovered. A third quantity of hydrocarbons released in response to crushing and thermo-vaporization in the crushing chamber is determined. A first hydrocarbon expulsion efficiency of the hydrocarbon source rock is determined as a ratio of a sum of the first quantity of hydrocarbons to a sum of the first quantity of hydrocarbons, the second quantity of hydrocarbons, and the third quantity of hydrocarbons. A powdered sample of the hydrocarbon source rock having a grain size less than or equal to substantially 250 microns is pyrolyzed. A fourth quantity of hydrocarbons released in response to performing open system pyrolysis on a powdered sample is determined. A second hydrocarbon expulsion efficiency of the hydrocarbon source rock is determined as a ratio of the first quantity of hydrocarbons to the fourth quantity of hydrocarbons. The hydrocarbon expulsion efficiency is provided as an input to a geological model capable of analyzing a hydrocarbon expulsion from the hydrocarbon source rock through geological history.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Laboratory artificial maturation studies by pyrolysis (heating of source rock sample in presence of inert atmosphere) depicting natural HC generation from source rocks are helpful. However, artificial maturation of kerogen by laboratory pyrolysis is far from representing maturation of the sedimentary organic matter in natural systems. The routine laboratory pyrolysis experiments are conducted either in closed or open systems, by isothermal or non-isothermal heating; in a hydrous or anhydrous reactors. Open system pyrolysis is conventionally conducted on a few milligrams of ground rock (usually less than 250 micronmeter) whereas close anhydrous systems can be micro-scale sealed vessel or gold-bag pyrolysis systems again utilizing small amount of ground rock or isolated kerogen. Powdered hydrocarbon source rock sample does not hold its original texture and porosity so fluid flow barriers no longer exist in powder sample. In open system anhydrous pyrolysis, the yields (generated HCs) are immediately removed from the system by carrier gas, whereas in the closed system pyrolysis, the yields remain in the system and are exposed to further heating (e.g., leading to secondary cracking). As a result, liquid hydrocarbons are retained and cracked to gas at higher experimental temperatures. On the other hand, hydrous pyrolysis (heating of kerogen in presence of excess water) can only be conducted in sealed reactors and this method also leads to secondary reactions and cracking of generated hydrocarbons within a pyrolysis chamber. With these analytical limitations of open system pyrolysis being completely open for all products to expel or a closed system that retains the generated products within the experimental chamber and result in hydrocarbon cracking and gas formation, it is clear that, none of the conventional pyrolysis systems can sufficiently simulate (approximate) the natural maturation processes. The system introduced here, because of cm size grain utilized, is in between the two available pyrolysis set ups and may be considered closer to a real (natural) system. The thermo-vaporization of the hydrocarbon source rock sample at 300° C. following pyrolysis has been reported to be sufficient to sweep retained hydrocarbons from the hydrocarbon source rocks samples.

This specification relates to determining hydrocarbon generation/retention/expulsion characteristics of hydrocarbons source rocks with emphasis on petroleum expulsion characteristics by use of open system pyrolysis and thermo-vaporization (at 375° C.) in a pyrolysis chamber followed by crushing and thermo-vaporization (at 375° C.) of hydrocarbon source rock sample in a crushing and thermo-vaporization chamber. Released hydrocarbons are first trapped and then analyzed by gas chromatography and/or gas chromatography mass spectrometry.

This specification describes methods and systems associated with the exploration for petroleum. In particular, this specification describes pyrolysis methods and systems to determine expulsion efficiency of hydrocarbons generated from hydrocarbon source rock. The pyrolysis methods and systems described here can be implemented in a laboratory and, in some implementations, the results obtained can be provided as inputs to computer-generated geological models used to study hydrocarbon generation and expulsion from hydrocarbon source rocks.

The expulsion of hydrocarbons from hydrocarbon source rock into reservoir rock, from which the hydrocarbon can be recovered, is affected by the release of generated hydrocarbons from kerogen and movement (that is, migration) of these hydrocarbons within the source rock. The release of liquid hydrocarbons from kerogen is controlled by the absorption or adsorption (or both) of the liquid hydrocarbons within or on the surface (or both) of the kerogen and diffusion of the hydrocarbons through kerogen. Thus, the efficiency of expulsion is controlled by the amount and oil-proneness (or hydrogen-richness) of kerogen.

The migration of oil within the source rock is affected by factors including, for example, an amount and type of organic matter, bitumen (oil) saturation threshold, effective migration paths in the hydrocarbon rock, pressure build-up and micro-fracturing, gas availability for the movement of oil in the gaseous phase, combinations of them, or other factors. These factors vary with the primary sedimentological conditions in the depositional environment of the source rock and secondary diagenetic processes during evolution of sedimentary basins. In other words, the mechanism of hydrocarbon migration will vary according to the lithofacies of the hydrocarbon source rock.

Laboratory pyrolysis is used to artificially mature kerogen and study the processes of hydrocarbon generation within and expulsion from the source rock. Laboratory pyrolysis experiments can be conducted in closed or open systems, by isothermal or non-isothermal heating of finely ground (for example, in powder form) hydrocarbon source rock samples, for example, in hydrous or anhydrous tubes. Open system pyrolysis can be conducted using, for example, a few milligrams of ground rock having a size equal to or less than approximately 250 micrometers. In open system pyrolysis, the yields (that is, the hydrocarbons expelled by pyrolysis) can be removed from the system (sometimes immediately after pyrolysis) by passing carrier gas. Closed system pyrolysis, for example, closed anhydrous systems, can be implemented in a micro-scale sealed vessel or implemented as gold-bag pyrolysis systems utilizing small amount of hydrocarbon source rock or isolated kerogen. In closed system pyrolysis, the generated hydrocarbons can remain in the system and be exposed to further heating until the end of pyrolysis, for example, until secondary cracking occurs. Hydrous pyrolysis involves heating of kerogen in presence of excess water. Such pyrolysis is conducted in sealed reactors and leads to secondary reactions and cracking of generated hydrocarbons within the pyrolysis chamber. Thus, different types of pyrolysis can be implemented to artificially mature kerogen to study the processes of hydrocarbon generation and migration. Such artificial kerogen maturation, while a useful tool, does not always accurately represent maturation of sedimentary organic matter in natural systems, that is, in the subsurface.

This disclosure describes an artificial kerogen maturation (and hydrocarbon generation from it as well as migration of generated hydrocarbons) technique that better approximates natural maturation of kerogen relative to the artificial kerogen maturation techniques described earlier. In some implementations, the artificial kerogen maturation technique described here can be implemented as a restricted system pyrolysis. The pyrolysis system is restricted in that, to be expelled due to pyrolysis, the hydrocarbons in the hydrocarbon source rock need to overcome a physical barrier before the hydrocarbons can reach a space from which the expelled hydrocarbons can be swept away by carrier gas. In other words, the restricted pyrolysis technique described in this specification studies the ability of the hydrocarbons in the rock sample to traverse through a physical barrier that is similar to the physical barrier that hydrocarbon generated during natural maturation would experience in the subsurface (for example, subsurface hydrocarbon reservoirs).

The techniques described here can be implemented to predict hydrocarbon accumulations or to predict hydrocarbons retained in hydrocarbon source rocks (or both). The techniques can also be implemented to determine an expulsion efficiency of hydrocarbons from hydrocarbon source rock samples, and to input such efficiency in computer-generated geological models, for example, models that can predict hydrocarbon accumulations. The expulsion efficiency obtained by implementing the techniques described here can increase a confidence in the computer-generated geographic models implemented in hydrocarbon exploration or recovery or both. For example, the expulsion efficiency can be used to calibrate petroleum system and basin modeling simulation which can lead to better understanding and determination of expulsion of hydrocarbons from source rock. The calibrated systems and simulations can be implemented to successfully discover hydrocarbon reservoirs, to better predict retained hydrocarbons in such reservoirs, or to identify sweet spots in unconventional resource estimation (or combinations of them). The time and effort in performing such processes can thereby be reduced to increase efficiency.

An open system pyrolysis apparatus is used for artificially maturing a hydrocarbon source rock sample, as well as separating and trapping hydrocarbon generated by maturation process. The hydrocarbon source rock sample can include fragments of the rock sample having an equivalent spherical diameter of substantially at least one centimeter (for example, ranging between 0.9 cm and several centimeters). The equivalent spherical diameter of the fragments of the rock sample is the diameter of a sphere having an equivalent volume as the rock sample. In some implementations, the hydrocarbon source rock sample can include multiple pieces of hydrocarbon rock at least some of which have the equivalent spherical diameter of substantially at least one centimeter. Some fragments can have an equivalent spherical diameter different from (that is, lesser than or greater than) at least one centimeter. In general, the hydrocarbon source rock sample can have a size that is substantially similar to the size of equivalent hydrocarbon rock that is found in the subsurface from which the rock sample is obtained.

The hydrocarbon source rock sample can be obtained from a hydrocarbon source rock to be studied. The grain size of hydrocarbon source rock in the subsurface affects a distance through which hydrocarbons generated and trapped in the rock need to traverse before being released during natural kerogen maturation. The hydrocarbon source rock sample is selected to have a grain size that is substantially similar to a grain size of hydrocarbon rock in the subsurface. In this manner, the experimental conditions of the artificial kerogen maturation can be made closer to the conditions of natural kerogen maturation. That is, in such conditions, the hydrocarbon in the rock sample will need to traverse a distance that is closer to the distance through which the hydrocarbons trapped in the rock need to traverse before being released during natural kerogen maturation. The hydrocarbon expulsion efficiency determined for the hydrocarbon source rock sample 104 following the artificial kerogen maturation will, consequently, be a more accurate prediction of the hydrocarbon expulsion efficiency of the hydrocarbon source rock in the subsurface following natural kerogen maturation.

Figure 3:
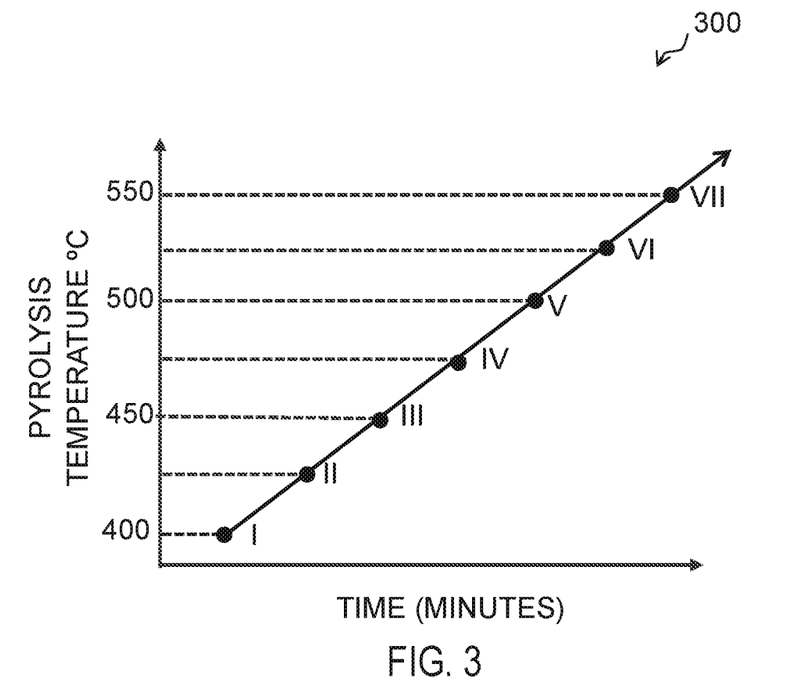
FIG. 3 is a plot of an example of pyrolysis temperature intervals (steps).

The pyrolysis chamber of an open system pyrolysis apparatus can be larger than conventional pyrolysis chambers used in the pyrolysis of hydrocarbon source rock samples. For example, the pyrolysis chamber can have a volume of substantially one liter (for example, ranging between 0.8 liters and few liters), and can be configured to hold several hundred grams (for example, up to nearly 800 g) of hydrocarbon source rock sample. The pyrolysis chamber can further be configured to heat the hydrocarbon source rock sample to temperatures as high as 650° C. In particular, the pyrolysis chamber can be configured to heat the hydrocarbon source rock sample at different temperature gradients and different temperature steps as described below with reference to FIG. 3 (only temperatures up to 550° C. are shown). Temperatures shown in FIG. 3 are final temperatures of pyrolysis windows, for instance 400° C. means a pyrolysis step with temperature range from 300 to 400° C. and a temperature of 425° C. means a pyrolysis step with temperature range from 300 to 425° C. and so on.

In some implementations, the hydrocarbon source rock sample can additionally be characterized in terms of the Total Organic Carbon (TOC) content as weight percent (wt %) of the source rock and determination of kerogen type using conventional organic geochemical techniques. The TOC content can be determined by LECO TOC analyzer where the organic carbon is measured after removal of carbonate carbon. The TOC content can also be determined by Source Rock Analyzers which have pyrolysis and oxidation ovens.

Figure 1:
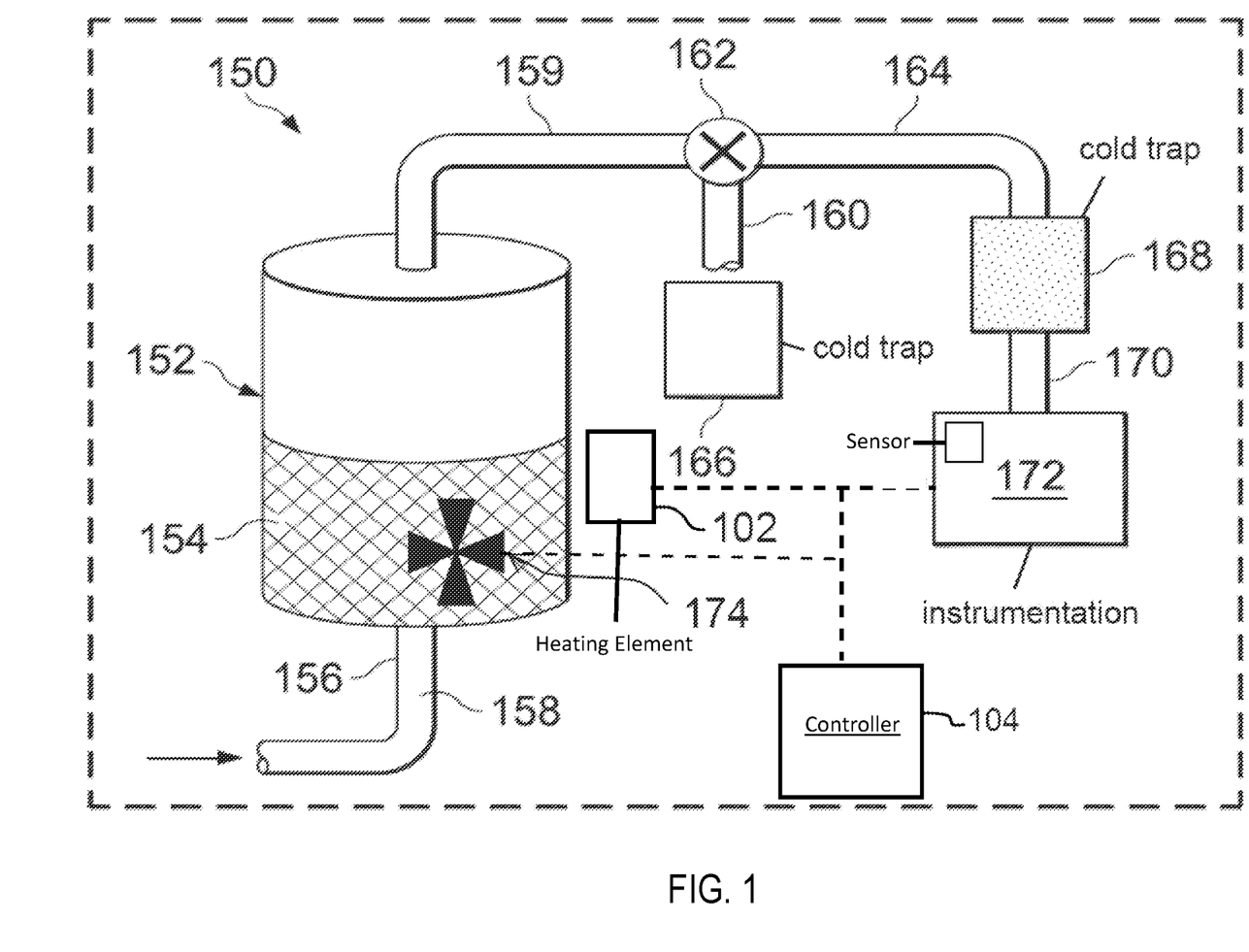
FIG. 1 is a schematic diagram of an example of a system for a Crushing and Thermo-vaporization chamber which will be utilized following open system pyrolysis of hydrocarbon source rock to crush and to liberate any trapped hydrocarbons.

FIG. 1 is a schematic diagram of an example of an integrated sample-crusher and thermo-vaporization apparatus 150. The apparatus 150 includes an integrated sample-crusher and thermo-vaporization chamber 152 in which the previously pyrolyzed hydrocarbon source rock sample is placed. In some implementations, this chamber can include a sample crusher apparatus (electric driven crushing blades 174), simultaneous to sample crushing, thermo-vaporization, a heating element 102, and a controller 104 that can control the heating element 102 to heat the pyrolyzed hydrocarbon source rock sample to a set temperature, such as 375° C. Crushing blades 174 can impact against the sample fragments while revolving.

In some implementations, a hydrocarbon transport (carrier gas) apparatus can be connected to the sample crushing and thermo-vaporization apparatus 150. For example, the hydrocarbon transport apparatus can include tubing 156 connected to a bottom side of the sample crushing and thermo-vaporization chamber 152. As described below, hydrocarbons transport 158 can be flowed through the thermo-vaporization chamber 152. The hydrocarbons recovery apparatus can also include tubing 159 connected to the thermo-vaporization chamber 152 (for example, on an upper side or other side) through which the hydrocarbons transport 158 can transport the hydrocarbons released during crushing and thermo-vaporization of the previously pyrolyzed hydrocarbon source rock sample 154 thermo-vaporization. The hydrocarbon transport (carrier gas) apparatus can include one or more valves (for example, valve 162) to control the flow of the recovered hydrocarbons. In some implementations, the apparatus can include additional tubing (for example, tubing 160, tubing 164, tubing 170) to transport all or portions of the recovered hydrocarbons to one or more cold traps. The apparatus can also be configured to flow all or portions of the recovered hydrocarbons to instrumentation 172 (for example, a chromatograph or other instrumentation) that is configured to analyze the hydrocarbons, for example, to determine chemical composition.

Figure 2:
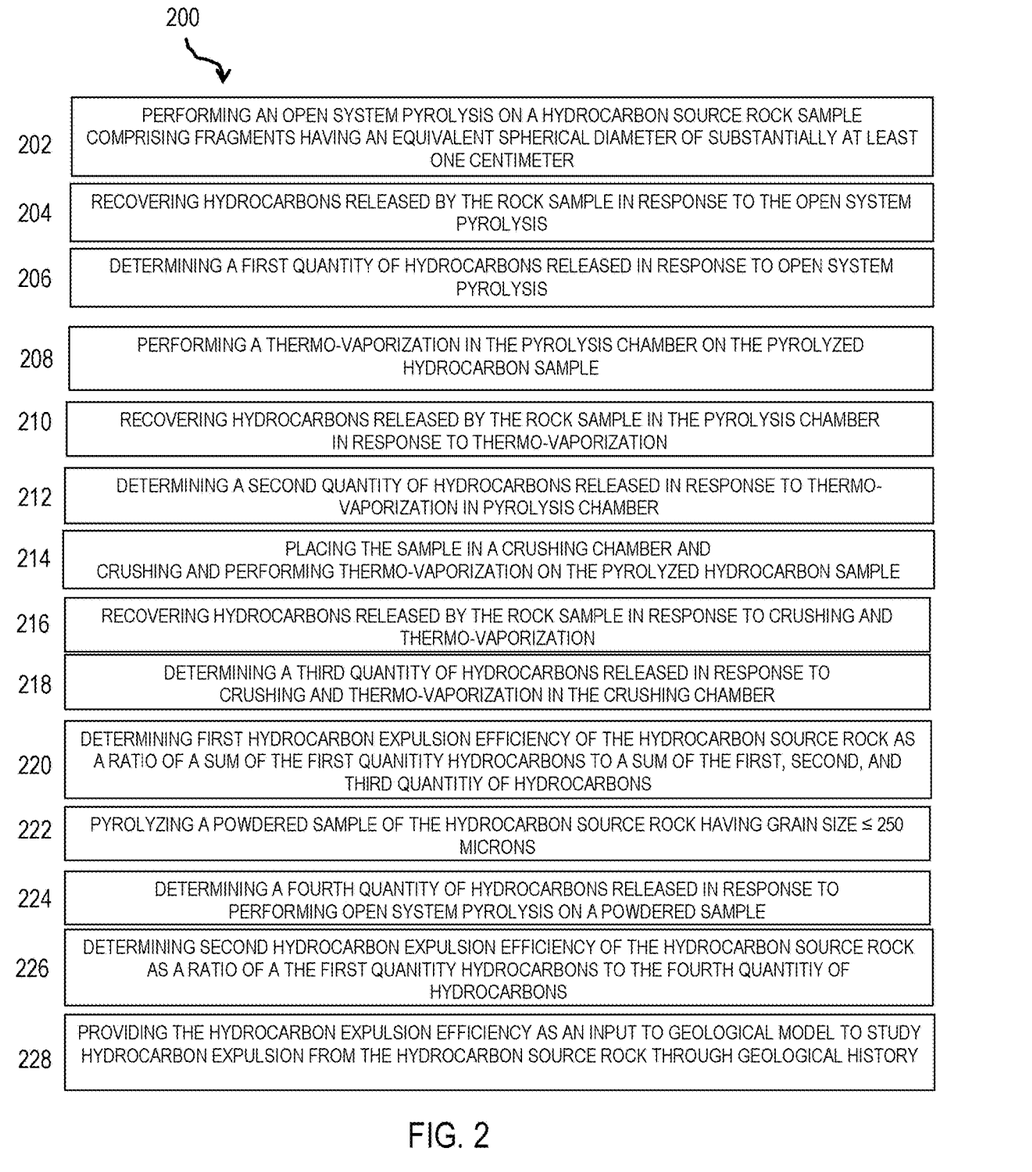
FIG. 2 is a flowchart of an example of a process for determining a hydrocarbon expulsion efficiency of hydrocarbon source rock.

FIG. 2 is a flowchart of an example of a process 200 for determining a hydrocarbon expulsion efficiency of hydrocarbon source rock. The process 200 can be implemented, for example, using the systems described above with reference to FIGS. 1A and 1B. At 202, an open system pyrolysis can be performed on fragments of a hydrocarbon source rock sample obtained from the subsurface. The hydrocarbon source rock sample can include fragments having an equivalent spherical diameter of substantially at least one centimeter. A pre-defined mass of the hydrocarbon source rock sample 104 used in open system pyrolysis can of a substantial enough quantity to be a representative sample of the source. That is, the sample can be of sufficient mass to counteract the effects of heterogeneity within the sample, such as a few hundred grams (for example, substantially 100 grams). During open system pyrolysis, the hydrocarbon source rock sample 104 is placed in the pyrolysis chamber 152 and heated non-isothermally. In some implementations, the temperature of the pyrolysis chamber 152 can be increased at different heating rates. FIG. 3 is a plot 300 of an example of pyrolysis temperature steps according to which the hydrocarbon source rock sample 104 can be pyrolyzed in the open system pyrolysis apparatus 100. For example, the temperature of the pyrolysis chamber 152 can be increased at a heating rate of substantially about 25° C. per minute (or lower or higher heating rates).

In some implementations, the pyrolysis can be conducted in multiple heating rates, for example, eight temperature stages (steps); from starting temperature of 300° C. to 400° C., from starting temperature of 300 to 425° C., and so on. The heating rate can be the same or different in each temperature stage. The increase in the heating rate between any consecutive temperature steps can be the same or different. For example, the increase in the heating gradient between consecutive temperature steps can remain 5° C. per minute for all temperature steps.

At 204, hydrocarbons released by the hydrocarbon source rock sample in response to the open system pyrolysis can be recovered. In some implementations, the pyrolysis chamber 152 can be continuously flushed with the inert hydrocarbons transport 108 (for example, helium or other inert gases) using the hydrocarbon transport apparatus. For example, the hydrocarbons transport 108 can be flowed into the pyrolysis chamber 152 through tubing 106 and out of the pyrolysis chamber 152 with the expelled hydrocarbons through tubing 110. As the hydrocarbons in the hydrocarbon source rock sample 104 are volatile in gaseous form at high temperatures, the hydrocarbons transport 108 can carry the expelled hydrocarbons out of the pyrolysis chamber 152. In some implementations, hydrocarbons expelled from the hydrocarbon source rock sample 104 can be flushed out of the pyrolysis chamber 152 after each temperature stage (e.g. from starting temperature of 300° C. to 450° C.). During a pyrolysis, both tubings 106 and 110 are continuously open to flush the expelled hydrocarbons.

The combination of the hydrocarbons and the hydrocarbons transport 108 can be flowed to one or more cold traps (for example, the cold trap 116 or the cold trap 118 or both). In some implementations, each cold trap can be a fused silica column submerged in a container filled with liquid nitrogen or other low temperature (for example, as low as −100° C.). Each cold trap can trap at least a portion of the hydrocarbons released by the hydrocarbon source rock sample either after open system pyrolysis or after thermo-vaporization. For example, the cold trap may not trap methane gas. At the end of any pyrolysis temperature step (for example, each temperature step, any one of the temperature steps, or the last temperature step), the cold trap can be heated first to a temperature of about 60° C. and then to an elevated temperature of about 375° C. for a set amount of time to purge the gaseous and liquid pyrolysis products, respectively. In this manner, the hydrocarbons trapped by the cold trap 118 can be released.

In some implementations, the hydrocarbon transport apparatus can be implemented to split the hydrocarbons carried by the hydrocarbons transport and flowing out of the pyrolysis chamber 152 into multiple streams. For example, the valve 162 can split the hydrocarbons transport flowing from the pyrolysis chamber 152 into a first gas stream and a second gas stream. The first gas stream can be directed to the removable cold trap 168 and the second portion can be directed to the cold trap 166. The first gas stream flowed through the removable cold trap 166 can then be flowed to another instrumentation (not shown) to determine a composition of the hydrocarbons. In some implementations, the first gas stream can be purged, for example, released to the atmosphere in a controlled vacuum hood. In some implementations, the gas stream exiting the pyrolysis chamber 152 can be split into multiple streams (that is, more than two streams). One of the streams can be flowed to the cold trap 168 and then to the instrumentation 172. Another stream can be flowed to the removable cold trap 166 and then to another instrumentation. A third stream can be purged, and so on. The splitting of the gas stream exiting the pyrolysis chamber 152 into multiple gas streams and the flow of the gas streams can be controlled, for example, using the valve 112.

At 206, a first quantity of hydrocarbons (A) released in response to performing the open system pyrolysis can be determined. In some implementations, the hydrocarbons carried by the hydrocarbons transport 159 out of the pyrolysis chamber 152 can be flowed to instrumentation 172 that can analyze composition of the expelled hydrocarbons. For example, the instrumentation 172 can include a sensor, such as a gas chromatograph (GC) or gas chromatography mass spectrometer (GC-MS). The instrumentation 172 can be implemented to characterize the hydrocarbons expelled from the hydrocarbon source rock sample 154. In some implementations, the instrumentation 172 can be implemented to quantify, for example, in micrograms of hydrocarbons per gram of hydrocarbon source rock sample. At 208, a thermo-vaporization is performed on the pyrolyzed hydrocarbon sample within pyrolysis chamber. At 210, hydrocarbons released by the hydrocarbon source rock sample in response to thermo-vaporization in the pyrolysis chamber can be recovered. At 212, a second quantity of hydrocarbons (B) released in response to performing the open system pyrolysis can be determined.

Figure 5A:
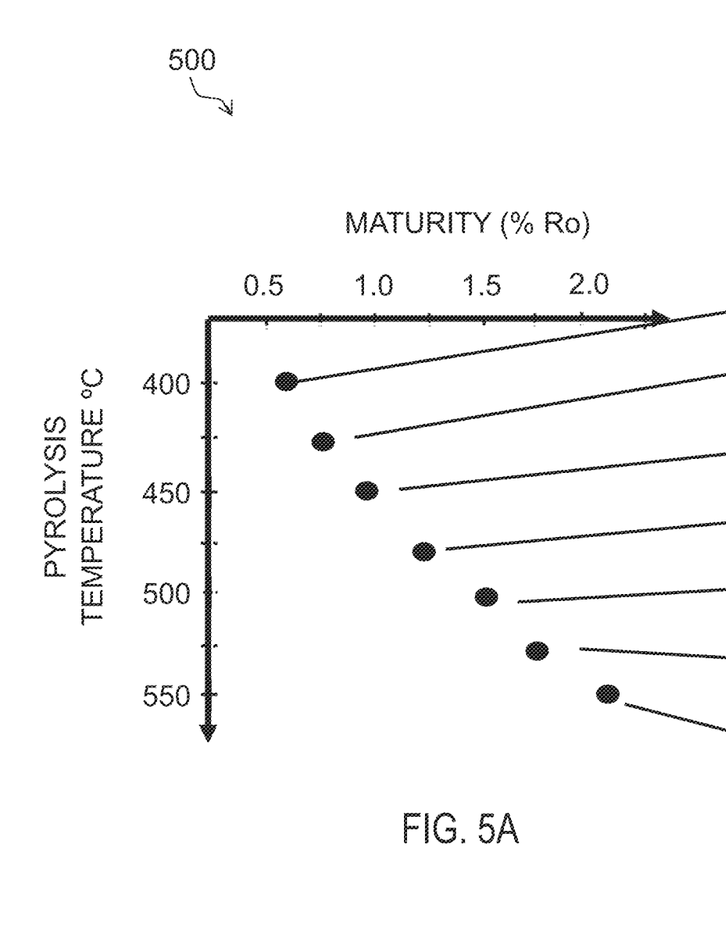
FIG. 5A is a plot of an example of maturity increase based on pyrolysis temperature steps.
Figure 5B:
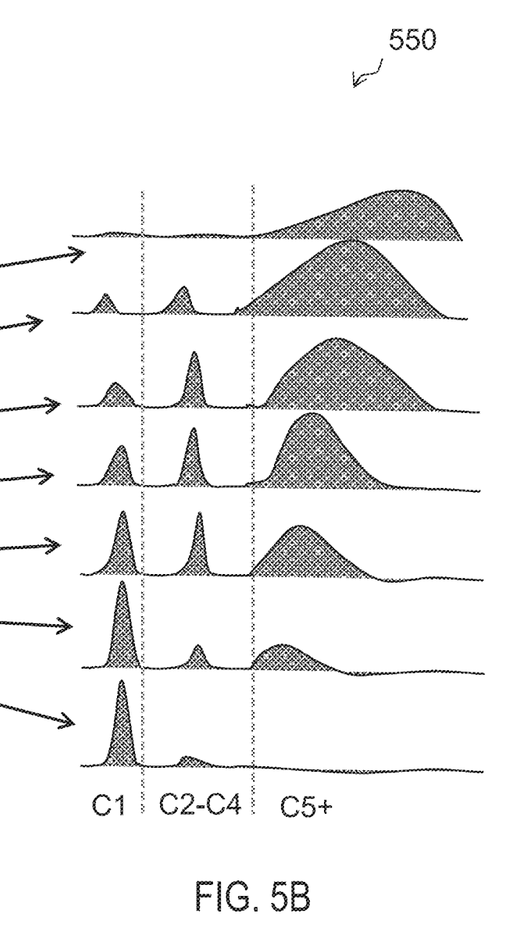
FIG. 5B is an example of hydrocarbon distributions recovered after pyrolysis and/or crushing-thermo-vaporization stage from a hydrocarbon source rock sample.

FIG. 5A is a plot of an example of pyrolysis temperature (only up to 550° C. are shown) to maturity increase of hydrocarbon source rock sample. FIG. 5B is an example of hydrocarbon class (methane, wet gas, light oil, heavy oil, etc.) distribution in hydrocarbons recovered from a hydrocarbon source rock sample. The two figures show the maturity of the residual organic matter within hydrocarbon source rock sample 152 reached at the end of each pyrolysis stage. The two figures also show with expected variations of hydrocarbon class distribution ($C_1$(methane), $C_2$-$C_4$ (ethane, propane and butane), $C_{5+}$ (pentane and heavier hydrocarbons)) with increasing maturity. That is, as the pyrolysis temperature stage increases, more maturity is attained and the lighter hydrocarbon class (for example, $C_1$-$C_4$) dominates.

Figure 4:
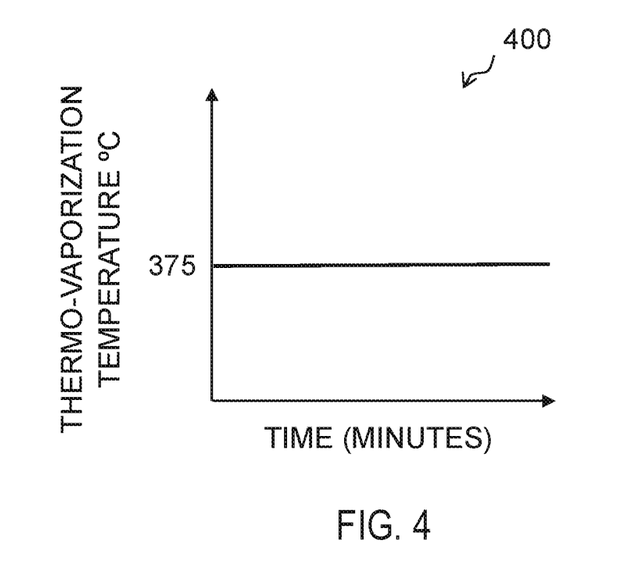
FIG. 4 is a plot of an example of a thermo-vaporization in a sample crushing chamber at a constant temperature.

At 214, a crushing and thermo-vaporization (within the thermo-vaporization chamber) at a temperature of 375° C. can be performed on the hydrocarbon source rock sample on which the open system pyrolysis was performed. In some implementations, after the open system pyrolysis, the hydrocarbon source rock sample is removed from the pyrolysis chamber 152, crushed and thermally vaporized. For example, the crushing and thermo-vaporization of the previously pyrolyzed hydrocarbon source rock sample can be performed simultaneously. During thermo-vaporization, the pyrolyzed hydrocarbon source rock sample 154 is placed in the crushing and thermo-vaporization chamber 152 and heated to 375° C. for a set amount of time. A quantity of the pyrolyzed hydrocarbon source rock sample 154 used in thermo-vaporization can be a few tens of grams (for example, substantially 20 g). FIG. 4 is a plot 400 of an example of a thermo-vaporization temperature gradient according to which the pyrolyzed hydrocarbon source rock sample 154 can be thermally vaporized in the thermo-vaporization apparatus 150. For example, the temperature of the chamber 152 can be kept constant at substantially 375° C. time. Thermo-vaporization can purge any retained hydrocarbons in the rock sample.

At 216, hydrocarbons released by the pyrolyzed hydrocarbon source rock sample in response to the crushing and thermo-vaporization can be recovered. In some implementations, the chamber 152 can be continuously flushed with the inert carrier gas 158 (for example, helium or other inert carrier gas) using the hydrocarbons recovery apparatus. For example, the carrier gas 158 can be flowed into the thermo-vaporization chamber 152 through tubing 156 and out of the chamber 152 with the expelled hydrocarbons through tubing 160. As the hydrocarbon in the pyrolyzed hydrocarbon source rock sample 154 breaks down into gaseous form, the carrier gas 158 can carry the expelled hydrocarbons out of the crushing and thermo-vaporization chamber 152. At 218, the third quantity of hydrocarbons (C) released in response to performing the open system pyrolysis can be determined.

The combination of the hydrocarbons and the carrier gas 158 can be flowed to one or more cold traps (for example, the cold trap 166 or the cold trap 168 or both). In some implementations, each cold trap can be a fused silica column submerged in a container filled with liquid nitrogen or other low temperature (for example, as low as −100° C.). At the end of thermo-vaporization, the cold trap can be heated first to a temperature of about 60° C. and then to an elevated temperature of about 375° C. to purge the gaseous and liquid pyrolysis products, respectively. In this manner, the hydrocarbons trapped by the cold trap 168 can be released.

Similar to gas stream splitting during open system pyrolysis, the hydrocarbons recovery apparatus can be implemented to split the hydrocarbons flowing out of the thermo-vaporization chamber 152 into multiple gas streams. For example, the valve 162 can split the gas flowing from the crushing and thermo-vaporization chamber 152 into a first gas stream and a second gas stream. The first gas stream can be directed to a removable cold trap 168 and the second portion can be directed to the cold trap 166. The first gas stream flowed through the removable cold trap 166 can then be flowed to another instrumentation (not shown) to determine a composition of the gas stream. In some implementations, the first gas stream can be purged, for example, released to atmosphere. In some implementations, the gas stream exiting the crushing and thermo-vaporization chamber 152 can be split into multiple streams (that is, more than two streams). One of the streams can be flowed to the cold trap 168 and then to the instrumentation 172. Another stream can be flowed to the removable cold trap 166 and then to another instrumentation. A third stream can be purged, and so on. The splitting of the gas stream exiting the crushing and thermo-vaporization chamber 152 into multiple gas streams and the flow of the gas streams can be controlled, for example, using the valve 162.

In some implementations, the hydrocarbons carried by the carrier gas 158 out of the crushing and thermo-vaporization chamber 152 can be flowed to instrumentation 172 that can analyze a composition of the expelled hydrocarbons. For example, the instrumentation 172 can include a gas chromatograph (GC) or gas chromatography-mass spectrometry (GC-MS). The instrumentation 172 can be implemented to characterize the hydrocarbons expelled from the pyrolyzed hydrocarbon source rock sample 154. In some implementations, the instrumentation 172 can be implemented to quantify, for example, in micrograms of hydrocarbons per gram of hydrocarbon source rock sample.

In the example implementations described above, the hydrocarbon source rock sample 104 was placed in a pyrolysis chamber 152 during open system pyrolysis, and the pyrolyzed hydrocarbon source rock sample 154 was then placed in a separate and distinct sample crushing and thermo-vaporization chamber 152 during thermo-vaporization. Alternatively, the pyrolysis chamber 152 can be used as the sample crushing and thermo-vaporization chamber 152. Upon completion of the open system pyrolysis, the pyrolyzed hydrocarbon source rock sample 154 can be placed in (or can remain in) the pyrolysis chamber 152. Sample crushing and thermo-vaporization of the pyrolyzed hydrocarbon source rock sample can then be performed as described above.

In some implementations, at the end of each step (that is, each pyrolysis temperature stage, thermo-vaporization), the maturity of the residual kerogen can be determined using procedures such as geochemical techniques (for example, vitrinite reflectance measurements, open system pyrolysis Tmax, or other geochemical techniques). In this manner, after each step, a determined maturity level for the source rock which has generated, expelled, or retained hydrocarbons can be characterized.

At 220, a first hydrocarbon expulsion efficiency of the hydrocarbon rock can be determined. For example, the efficiency can be determined as a ratio of a sum of the first quantity of hydrocarbons (i.e., the hydrocarbons released during open system pyrolysis of the hydrocarbon source rock sample 104—$HC_{Pyrolysis}$) to the sum of the first, the second (from thermo-vaporization at 375° C. in the pyrolysis chamber 152—$HC_{Thermo\text{-}vaporization}$), and third (i.e., the hydrocarbons released during crushing and thermo-vaporization at 375° C. of the pyrolyzed hydrocarbon source rock sample 154—$HC_{CrushingThermo\text{-}Vaporization}$). In some implementations, the hydrocarbon expulsion efficiency (HCEE) can be determined using Equation 1 shown below.

$$HCEE = (HC_{Pyrolysis}) \times 100 / (HC_{Pyrolysis} + HC_{Thermo\text{-}Vaporization} + HC_{CrushingThermo\text{-}Vaporization}) \quad \text{(Equation 1)}$$

In Equation 1, $HC_{Pyrolysis}$ is the quantity (for example, in micrograms per gram of sample) of hydrocarbons released in response to open system pyrolysis of the hydrocarbon source rock sample 104. $HC_{Thermo\text{-}Vaporization}$ is the quantity (for example, in micrograms per gram of sample) of hydrocarbons released in response to thermo-vaporization of previously pyrolyzed hydrocarbon source rock sample 104. $HC_{CrushingThermo\text{-}Vaporization}$ is the quantity (for example, in micrograms per gram of sample) of hydrocarbons released in response to crushing and thermo-vaporization of the previously pyrolyzed hydrocarbon source rock sample 154.

At 222, a second hydrocarbon source rock sample can be obtained from the same hydrocarbon source rock from which the hydrocarbon source rock sample 104 can be obtained. The rock sample can be ground to have grain sizes in the micrometer range (for example, less than substantially 250 µm). At 222, an open system pyrolysis can be performed on the powdered rock sample. A quantity of the powder size hydrocarbon source rock sample for the open system pyrolysis can be a few hundreds of milligrams to one gram (for example, substantially less than 1 gram). The open system pyrolysis on the second hydrocarbon rock sample can be performed using the open system pyrolysis apparatus 100 using techniques similar to those described above.

At 224, a fourth quantity of hydrocarbons released in response to performing the open system pyrolysis of the powder hydrocarbon source rock sample can be determined using techniques similar to those described above.

At 226, as a verification of the first HCEE found by using Equation 1, the second HCEE can also be determined using Equation 2 shown below.

$$HCEE = (HC_{Pyrolysis}) \times 100/HC_{PowderedSamplePyrolysis} \quad \text{(Equation 2)}$$

In Equation 2, $HC_{Pyrolysis}$ is the quantity (for example, in micrograms per gram of sample) of hydrocarbons released in response to open system pyrolysis of the hydrocarbon source rock sample 104, and $HC_{PowderedSamplePyrolysis}$ is the quantity (for example, in micrograms per gram of sample) of hydrocarbons released in response to open system pyrolysis of the powdered hydrocarbon source rock sample 104. HCCE calculated here is based on the ratio of hydrocarbons released from pyrolysis of chip grain size (e.g., 1 cm) of the hydrocarbon source rock to hydrocarbons released from pyrolysis of powder form of the same hydrocarbon source rock. Hydrocarbon expulsion efficiency in case of powdered sample is considered to be not effected by any barriers and the amount of hydrocarbons released is assume to be maximum (e.g., hydrocarbons generated equals hydrocarbon released from the hydrocarbon source rock). It is expected that hydrocarbons released from pyrolysis of chip grain size (e.g., 1 cm) of the same hydrocarbon source rock sample will be comparatively less and the HCCE will be less than 100%.

At 228, the hydrocarbon expulsion efficiency can be provided as an input to a geological model to study hydrocarbon expulsion from the hydrocarbon source rock through geological history.

Figure 6:
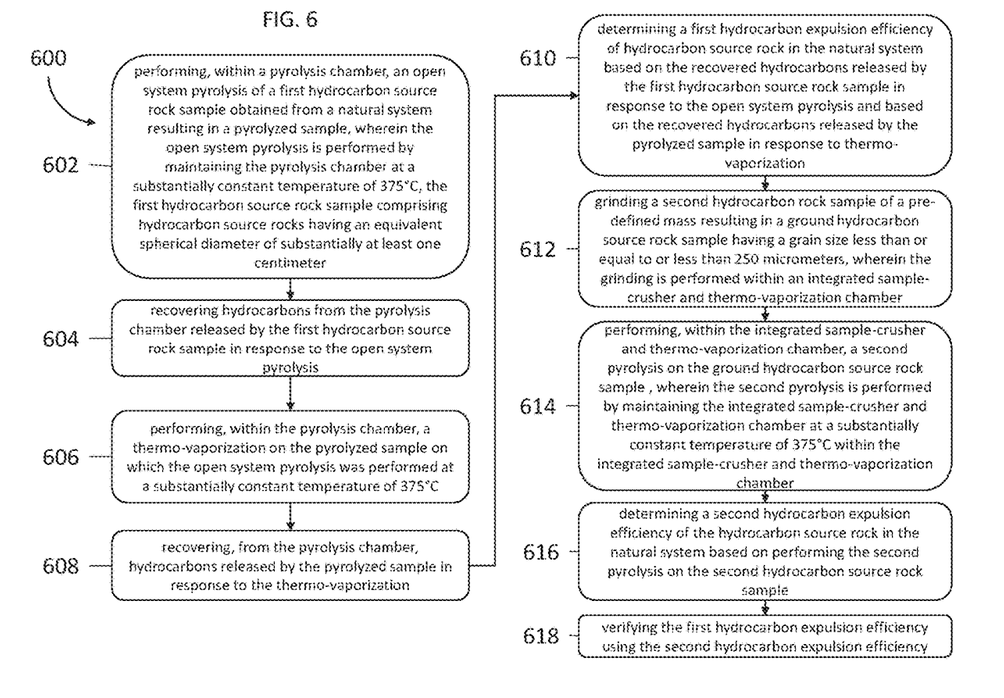
FIG. 6 is a flowchart of another example of a process for determining a hydrocarbon expulsion efficiency of hydrocarbon source rock.

FIG. 6 shows a flowchart of another example method 600 for determining a hydrocarbon expulsion efficiency of hydrocarbon source rock. At 602, an open system pyrolysis of a first hydrocarbon source rock sample obtained from a natural system is performed within a pyrolysis chamber. This results in a pyrolyzed sample. The open system pyrolysis is performed by maintaining the pyrolysis chamber at a substantially constant temperature of 375° C. The first hydrocarbon source rock sample includes hydrocarbon source rocks having an equivalent spherical diameter of at least substantially one centimeter. At 604, hydrocarbons released by the first hydrocarbon source rock sample are recovered from the pyrolysis chamber in response to the open system pyrolysis. At 606, a thermo-vaporization is performed (within the pyrolysis chamber) on the pyrolyzed sample on which the open system pyrolysis was performed at a substantially constant temperature of 375° C. At 608, hydrocarbons released by the pyrolyzed sample are recovered from the pyrolysis chamber in response to the thermo-vaporization. At 610, a first hydrocarbon expulsion efficiency of hydrocarbon source rock in the natural system is determined based on the recovered hydrocarbons released by the first hydrocarbon source rock sample in response to the open system pyrolysis and based on the recovered hydrocarbons released by the pyrolyzed sample in response to thermo-vaporization. At 612, a second hydrocarbon rock sample of a pre-defined mass is ground resulting in a ground hydrocarbon source rock sample having a grain size less than or equal to or less than 250 micrometers. The grinding is performed within an integrated sample-crusher and thermo-vaporization chamber. At 614, a second pyrolysis is performed (within the integrated sample-crusher and thermo-vaporization chamber) on the ground hydrocarbon source rock sample. The second pyrolysis is performed by maintaining the integrated sample-crusher and thermo-vaporization chamber at a substantially constant temperature of 375° C. within the integrated sample-crusher and thermo-vaporization chamber. At 616, a second hydrocarbon expulsion efficiency of the hydrocarbon source rock in the natural system is determined based on performing the second pyrolysis on the second hydrocarbon source rock sample. At 618, the first hydrocarbon expulsion efficiency is verified using the second hydrocarbon expulsion efficiency.

In sum, the artificial maturation of hydrocarbon source rock samples using the techniques described in this specification can lead to better understanding of expulsion and retention of hydrocarbons in hydrocarbon source rocks in natural systems. Better understanding and quantification of expelled hydrocarbons versus retained hydrocarbons (with increasing maturation in laboratory experiments) can be quantified and converted into parameters. Such parameters can be provided as input to geological models, for example, basin modeling software, to calibrate the expulsion-retention of hydrocarbons that are generated during burial and maturation of hydrocarbon source rocks.

Thus, particular implementations of the subject matter have been described. Other implementations are within the scope of the following claims.

The invention claimed is:

1. A system comprising:
   an integrated sample-crusher and thermo-vaporization chamber configured to retain a hydrocarbon rock sample;
   a heating element configured to heat the integrated sample-crusher and thermo-vaporization chamber;
   a sensor configured to detect hydrocarbons released within the integrated sample-crusher and thermo-vaporization chamber;
   a controller configured to control the heating element to a set temperature for a set amount of time, the controller configured to control the integrated sample-crusher, the controller configured to:
      heat the integrated sample-crusher and thermo-vaporization chamber, by the heating element, to a temperature of substantially 375° C.;
      maintain, within the integrated sample-crusher and thermo-vaporization chamber, a constant temperature of substantially 375° C., by the heating element, while the integrated sample-crusher and thermo-vaporization chamber is in use;
      determine a first hydrocarbon expulsion efficiency of hydrocarbon source rock in a natural system based on recovered hydrocarbons released by a first hydrocarbon source rock sample in response to the maintained temperature, the amount of recovered hydrocarbons determined by the sensor and interpreted by the controller;
      grind a second hydrocarbon rock sample of a pre-defined mass resulting in a ground hydrocarbon source rock sample having a grain size less than or equal to 250 micrometers, wherein the grinding is performed within the integrated sample-crusher and thermo-vaporization chamber;
      re-heat the integrated sample-crusher and thermo-vaporization chamber to a temperature of substantially 375° C.;
      maintain, within the integrated sample-crusher and thermo-vaporization chamber, a constant temperature of substantially 375° C. while the integrated sample-crusher and thermo-vaporization chamber contains the second hydrocarbon rock sample in the ground state;

determine a second hydrocarbon expulsion efficiency of the hydrocarbon source rock in the natural system based maintaining the temperature on the second hydrocarbon source rock sample, the amount of recovered hydrocarbons determined by the sensor and interpreted by the controller; and verify the first hydrocarbon expulsion efficiency using the second hydrocarbon expulsion efficiency.

2. The system of claim 1, wherein the integrated sample-crusher and thermo-vaporization chamber comprises electrically driven grinding blades.

3. The system of claim 1, wherein the integrated sample-crusher and thermo-vaporization chamber is configured to contain a sample size of at least 100 grams.

4. The system of claim 1, wherein the integrated sample-crusher and thermo-vaporization chamber has a volume of at least 1 liter.

* * * * *